United States Patent
Metz et al.

(10) Patent No.: US 8,673,644 B2
(45) Date of Patent: Mar. 18, 2014

(54) SERUM MARKERS FOR TYPE II DIABETES MELLITUS

(75) Inventors: Thomas O. Metz, Kennewick, WA (US); Wei-Jun Qian, Richland, WA (US); Jon M. Jacobs, Pasco, WA (US); Ashoka D. Polpitiya, Richland, WA (US); David G. Camp, II, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 375 days.

(21) Appl. No.: 12/120,043

(22) Filed: May 13, 2008

(65) Prior Publication Data

US 2009/0286324 A1 Nov. 19, 2009

(51) Int. Cl.
*G01N 33/00* (2006.01)
*G01N 33/48* (2006.01)

(52) U.S. Cl.
USPC .................................. 436/63; 436/86; 436/87

(58) Field of Classification Search
None
See application file for complete search history.

(56) References Cited

U.S. PATENT DOCUMENTS

| | | | |
|---|---|---|---|
| 2006/0134699 A1* | 6/2006 | Jackowski et al. | 435/7.1 |
| 2006/0160232 A1* | 7/2006 | Jackowski et al. | 436/86 |
| 2008/0057590 A1* | 3/2008 | Urdea et al. | 436/71 |
| 2008/0188004 A1* | 8/2008 | Walsh et al. | 436/86 |

FOREIGN PATENT DOCUMENTS

| | | |
|---|---|---|
| JP | 2005-525535 A | 8/2005 |
| WO | WO 03/046004 A2 | 6/2003 |
| WO | 2005024429 A1 | 3/2005 |

OTHER PUBLICATIONS

Metz, Thomas O., et al., Application of Proteomics in the Discovery of Candidate Protein Biomarkers in a Diabetes Autoantibody Standardization Program Sample Subset, Journal of Proteome Research, 2008, vol. 7, 698-707 pps.
Metz, Thomas O., et al., Identification of Biomarkers of Type 1 Diabetes Mellitus Utilizing Capillary LC-FTICR MS and the Accurate Mass and Time Tag (AMT) Approach, U.S. HUPO Conference, Mar. 5-Mar. 9, 2007, Seattle, WA.
Extended European Search Report for International Application No. PCT/US2009/043794, dated May 20, 2011.
Ahmad, J. et al., A Study of Plasma Alpha-s-Macroglobulin Levels in Type 2 Diabetic Subjects with Microalbuminuria, Journal of Association of Physicians of India, Association of Physicians of India, Bombay, IN, vol. 49, Nov. 11, 2001, pp. 1062-1065.

* cited by examiner

*Primary Examiner* — Dirk Bass
(74) *Attorney, Agent, or Firm* — Klarquist Sparkman, LLP

(57) ABSTRACT

A method for identifying persons with increased risk of developing type 2 diabetes mellitus utilizing selected biomarkers described hereafter either alone or in combination. The present invention allows for broad based, reliable, screening of large population bases and provides other advantages, including the formulation of effective strategies for characterizing, archiving, and contrasting data from multiple sample types under varying conditions.

4 Claims, No Drawings

SERUM MARKERS FOR TYPE II DIABETES MELLITUS

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy. The Government has certain rights in the invention.

BACKGROUND OF THE INVENTION

1. Field of the Invention

The present invention generally relates to methods and systems for the screening and detection of disease and more particularly to methods and systems for the screening and detection of persons at risk for developing type II diabetes mellitus.

2. Background of the Invention

Type II diabetes mellitus is a life changing disease that affects millions of persons. While the disease may be clinically diagnosed and confirmed fairly easily in some cases, earlier detection may lead to the possibility of intervention(s) that would alter or lessen the onset of clinical symptoms or allow other forms of preventative care to be undertaken.

Currently, one of the best approaches for predicting who may be at risk for developing type II diabetes mellitus before onset of clinical symptoms is by the oral glucose tolerance test (OGTT). The OGTT, is inconvenient, requires fasting and is not highly reproducible. The fasting blood glucose (FBG) is less burdensome, but much less sensitive, particularly in older Americans who have the highest prevalence of diabetes and pre-diabetes. The quantitation of Hemoglobin A1c (a glycated form of hemoglobin) from blood has been widely used as a test for assessing the adequacy of glycemic control and risk of complications in diabetic patients, but this test is not sufficiently sensitive to detect the range of glucose values typically seen in pre-diabetes or new onset type II diabetes. Furthermore, there are many variants of hemoglobin present in blood. This is particularly applicable in minority populations disproportionately affected by diabetes, and this adds additional uncertainty to the use of this test. A simplified, less burdensome approach to the diagnosis of diabetes and pre-diabetes would facilitate increased recognition and improved care of these individuals. While progress has been made to improve the accuracy and reproducibility of the measurement of surrogate biomarkers predictive of those at high risk for developing type II diabetes, a set of candidate biomarkers would benefit the clinical community, particularly if such surrogate biomarkers result in higher sensitivity and specificity.

Accordingly, what is needed is a method and system of screening for persons with increased risk of developing type II diabetes mellitus that utilizes candidate biomarkers allowing for broad based, reliable screening of large population bases. In addition, effective strategies for characterizing, archiving, and contrasting data from multiple sample types under varying conditions (e.g. control versus disease) are also needed.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY OF THE INVENTION

The present application describes a method for identifying persons with increased risk of developing type II diabetes mellitus utilizing selected biomarkers described hereafter either alone or in combination. The present invention allows for broad based, reliable screening of large population bases and provides other advantages including the formulation of effective strategies for characterizing, archiving, and contrasting data from multiple sample types under varying conditions. In one embodiment of the present invention, the markers are selected from the following:

```
(1) 163 kDa protein; peptide sequences:
LVHVEEPHTETVRK, MVSGFIPLKPTVK, DLKPAIVK,
DMYSFLEDMGLK, NEDSLVFVQTDK, SASNMAIVDVK,
TEHPFTVEEFVLPK, TTVMVK, FQVDNNNR, ATVLNYLPK,
RKEYEMK, DTVIKPLLVEPEGLEK (2) 45 kDa protein; peptide sequences:
DKVNSFFSTFK, LTPYADEFKVK (3) afamin; peptide sequences:
RHPDLSIPELLR, HFQNLGK (4) alpha-2-macroglobulin; peptide sequences:
SASNMAIVDVK, RKEYEMK, ATVLNYLPK, FQVDNNNR,
DTVIKPLLVEPEGLEK, TEHPFTVEEFVLPK, NEDSLVFVQTDK,
DMYSFLEDMGLK, DLKPAIVK, MVSGFIPLKPTVK,
LVHVEEPHTETVRK, TTVMVK (5) apolipoprotein A-I; peptide sequences:
AHVDALR, SGRDYVSQFEGSALGK, PYLDDFQKK,
YVSQFEGSALGK, LHELQEK, VSFLSALEEYTK, QKLHELQEK (6) apolipoprotein A-IV; peptide sequences:
DKVNSFFSTFK, LTPYADEFKVK (7) apolipoprotein B-100; peptide sequences:
MLETVR, AVSMPSFSILGSDVR, TEVIPPLIENR, SVGFHLPSR (8) complement C4B1; peptide sequences:
GQIVFMNREPK, GPEVQLVAHSPWLK, SHALQLNNR,
DFALLSLQVPLKDAK, YIYGKPVQGVAYVR (9) ceruloplasmin; peptide sequences:
AETGDKVYVHLK, GPEEEHLGILGPVIWAEVGDTIR

(10) clusterin isoform 1; peptide sequences:
TLLSNLEEAK, FMETVAEK

(11) clusterin; peptide sequences:
TLLSNLEEAK, FMETVAEK

(12) complement C3; peptide sequences:
FYYIYNEK, LMNIFLK, IPIEDGSGEVVLSR, IWDVVEK,
TIYTPGSTVLYR, KGYTQQLAFR, RIPIEDGSGEVVLSR,
VQLSNDFDEYIMAIEQTIK, RQGALELIKK, AAVYHHFISDGVRK,
YYTYLIMNK

(13) complement C4; peptide sequences:
GPEVQLVAHSPWLK, SHALQLNNR, DFALLSLQVPLKDAK,
YIYGKPVQGVAYVR, GQIVFMNREPK

(14) complement C4A; peptide sequences:
GPEVQLVAHSPWLK, SHALQLNNR, DFALLSLQVPLKDAK,
YIYGKPVQGVAYVR, GQIVFMNREPK

(15) complement C4B; peptide sequences:
YIYGKPVQGVAYVR, GQIVFMNREPK, SHALQLNNR,
GPEVQLVAHSPWLK, DFALLSLQVPLKDAK
```

-continued

(16) FGA protein; peptide sequences:
DSHSLTTNIMEILR, GLIDEVNQDFTNR,
LKNSLFEYQK

(17) gelsolin isoform b; peptide sequences:
HVVPNEVVVQR, TASDFITK

(18) gelsolin; peptide sequences:
HVVPNEVVVQR, TASDFITK

(19) hemopexin; peptide sequences:
LWWLDLK, RLWWLDLK,
GDKVWVYPPEKK

(20) histidine-rich glycoprotein; peptide
sequences:
DSPVLIDFFEDTER, ADLFYDVEALDLESPK

(21) Hypothetical protein DKFZp779N0926; peptide
sequences:
RLDGSVDFK, TSTADYAMFK

(22) Inter-alpha-trypsin inhibitor heavy chain H2
precursor; peptide sequences:
FYNQVSTPLLR, SLAPTAAAK, TILDDLR

(23) pregnancy zone protein; peptide sequences:
MVSGFIPLKPTVK, DLKPAIVK, ATVLNYLPK

(24) Similar to fibrinogen, A alpha polypeptide;
peptide sequences:
LKNSLFEYQK, DSHSLTTNIMEILR, GLIDEVNQDFTNR

(25) Splice Isoform 1 of Inter-alpha-trypsin
inhibitor heavy chain H4; peptide sequences:
NVVFVIDK, LGVYELLLK, ETLFSVMPGLK

(26) Splice Isoform 2 of Inter-alpha-trypsin
inhibitor heavy chain H4; peptide sequences:
LGVYELLLK, ETLFSVMPGLK, NVVFVIDK

(27) Splice Isoform Alpha of Fibrinogen alpha/
alpha-E chain; peptide sequences:
MELERPGGNEITR, LKNSLFEYQK, DSHSLTTNIMEILR,
TVIGPDGHKEVTK, GLIDEVNQDFTNR

(28) Splice Isoform Alpha-E of Fibrinogen alpha/
alpha-E chain; peptide sequences:
LKNSLFEYQK, DSHSLTTNIMEILR, MELERPGGNEITR,
GLIDEVNQDFTNR, TVIGPDGHKEVTK

(29) Splice Isoform Gamma-A of Fibrinogen gamma
chain; peptide sequences:
RLDGSVDFK, TSTADYAMFK

(30) Splice Isoform Gamma-B of Fibrinogen gamma
chain; peptide sequences:
RLDGSVDFK, TSTADYAMFK

(31) Vitamin D-binding protein; peptide sequences:
ELPEHTVK, KFPSGTFEQVSQLVK, THLPEVFLSK, HLSLLTTLSNR The presence of the markers described herein may be determined and utilized in a variety of ways employing various methodologies and utilizing a variety of sample types. Thus while one embodiment of the invention related to the application of the markers of the present invention in serum or plasma is described, this description is intended to be illustrative only and not exclusive in any way. With appropriate modification such a method may also be utilized in other sample types. In this and comparing the quantity of the at least one serum constituent to a standardized range of levels for this constituent to determine whether the level of the serum constituent when compared to the normal range is indicative of a predisposition for type II diabetes mellitus. A system for performing the method of the present invention is made up of the requisite pieces and parts that would allow such a method to be performed.

DETAILED DESCRIPTION OF THE PREFERRED EMBODIMENT OF THE INVENTION

In one embodiment of the present invention, the method for determining whether a person has an increased risk of developing type II diabetes mellitus involves the testing of human plasma or serum samples for the presence of the aforementioned biomarkers. Thus after plasma or serum is collected and appropriately processed, testing for the presence of these biomarkers is performed by capillary liquid chromatography-Fourier transform ion cyclotron resonance mass spectrometry of protein digests of these human plasma and serum samples. While these methods have been described and were utilized in testing, it is to be distinctly understood that the invention is not limited to any particular form of testing utilized, but is intended to include all methods that are capable of detecting the materials that are set forth in the claims.

In one particular embodiment of the invention, the method employed the testing of samples for the presence of the following proteins selected from the group of 31 set forth previously. This select group included the following:

(1) 163 kDa protein; peptide sequences:
LVHVEEPHTETVRK, MVSGFIPLKPTVK, DLKPAIVK,
DMYSFLEDMGLK, NEDSLVFVQTDK, SASNMAIVDVK,
TEHPFTVEEFVLPK, TTVMVK, FQVDNNNR, ATVLNYLPK,
RKEYEMK, DTVIKPLLVEPEGLEK (2) 45 kDa protein; peptide sequences:
DKVNSFFSTFK, LTPYADEFKVK (3) alpha-2-macroglobulin; peptide sequences:
SASNMAIVDVK, RKEYEMK, ATVLNYLPK, FQVDNNNR,
DTVIKPLLVEPEGLEK, TEHPFTVEEFVLPK, NEDSLVFVQTDK,
DMYSFLEDMGLK, DLKPAIVK, MVSGFIPLKPTVK,
LVHVEEPHTETVRK, TTVMVK (4) apolipoprotein B-100; peptide sequences:
MLETVR, AVSMPSFSILGSDVR TEVIPPLIENR, SVGFHLPSR (5) complement C4B1; peptide sequences:
GQIVFMNREPK, GPEVQLVAHSPWLK, SHALQLNNR,
DFALLSLQVPLKDAK, YIYGKPVQGVAYVR (6) ceruloplasmin; peptide sequences:
AETGDKVYVHLK, GPEEEHLGILGPVIWAEVGDTIR (7) complement C3; peptide sequences:
FYYIYNEK, LMNIFLK, IPIEDGSGEVVLSR, IWDVVEK,
TIYTPGSTVLYR, KGYTQQLAFR, RIPIEDGSGEVVLSR,
VQLSNDFDEYIMAIEQTIK, RQGALELIKK, AAVYHHFISDGVRK,
YYTYLIMNK (8) complement C4; peptide sequences:
GPEVQLVAHSPWLK, SHALQLNNR, DFALLSLQVPLKDAK,
YIYGKPVQGVAYVR, GQIVFMNREPK (9) complement C4B; peptide sequences:
YIYGKPVQGVAYVR, GQIVFMNREPK, SHALQLNNR,
GPEVQLVAHSPWLK, DFALLSLQVPLKDAK The results of this testing in non-diabetic, diabetic and control samples showed the presence of each of these proteins at significantly elevated levels in persons diagnosed with type II diabetes, while the normal and control samples did not have these elevated levels. Thus a method wherein human serum or plasma is tested for at least one protein from this list serves as an effective predictive or diagnostic screen or test for type II diabetes. In addition, the above listed proteins can be further explored in targeted proteomic studies utilizing isotopically-labeled peptide internal standards for absolute quantitation, which will enable the determination of laboratory-defined sensitivity and specificity with blinded samples. Further embodiments of the invention may also be made by combining various of these proteins, either alone or in combination with other biomarkers.

Various methods for performing the quantitative and qualitative analysis of these proteins may be utilized. In one preferred embodiment of the invention, LC-MS/MS analyses were performed, however it is to be distinctly understood that the invention is not limited thereto. Any reliable manner of performing quantitative or qualitative analysis of a sample for the presence and quantity of any of the preselected biomarkers previously set forth and discussed may be utilized.

The purpose of the foregoing is to enable the United States Patent and Trademark Office and the public generally, especially the scientists, engineers, and practitioners in the art who are not familiar with patent or legal terms or phraseology, to determine quickly from a cursory inspection, the nature and essence of the technical disclosure of the application. The abstract is neither intended to define the invention of the application, which is measured by the claims, nor is it intended to be limiting as to the scope of the invention in any way.

What is claimed is:

1. A method of identifying a human subject's risk for developing type II diabetes mellitus or diagnosing type II diabetes mellitus in a human subject, comprising:

Analyzing a serum or blood plasma sample of said human subject to determine the quantity of:
(1) 163 kDa protein;
(2) 45 kDa protein;
(3) alpha-2-macroglobulin;
(4) apolipoprotein B-100;
(5) complement C4B1;
(6) ceruoplasmin;
(7) complement C3;
(8) complement C4;
(9) complement C4B;
(10) afamin;
(11) apolipoprotein A-1;
(12) apolipoprotein A-IV;
(13) clusterin isoform 1;
(14) clusterin;
(15) complement C4A;
(16) FGA protein;
(17) gelsolin isoform b;
(18) gelsolin;
(19) hemopexin;
(20) histidine-rich glycoprotein;
(21) hypothetical protein DKFZp779N0926;
(22) inter-alpha-trypsin inhibitor heavy chain H2 precursor;
(23) pregnancy zone protein;
(24) similar to fibrinogen, A alpha polypeptide;
(25) splice isoform 1 of inter-alpha-trypsin inhibitor heavy chain H4;
(26) splice isoform 2 of inter-alpha-trypsin inhibitor heavy chain H4;
(27) splice isoform Alpha of fibrinogen alpha/alpha-E chain;
(28) splice isoform Alpha-E of fibrinogen alpha/alpha-E chain;
(29) splice isoform Gamma-A of fibrinogen gamma chain;
(30) splice isoform Gamma-B of fibrinogen gamma chain; and
(31) vitamin D-binding protein;

Determining if the proteins are upregulated or downregulated relative to a subject not having type II diabetes mellitus; and Identifying the human subject as having an increased risk for developing type II diabetes or diagnosing the human subject with type II diabetes if at least one of the proteins are upregulated or downregulated relative to the subject not having type II diabetes mellitus.

2. The method of claim 1, wherein the proteins are detected by detecting:

one or more of LVHVEEPHTETVRK (SEQ ID NO: 1), MVSGFIPLKPTVK (SEQ ID NO: 2), DLKPAIVK (SEQ ID NO: 3), DMYSFLEDMGLK (SEQ ID NO: 4), NEDSLVFVQTDK (SEQ ID NO: 5), SASNMAIVDVK (SEQ ID NO: 6), TEHPFTVEEFVLPK (SEQ ID NO: 7), TTVMVK (SEQ ID NO: 8), FQVDNNNR (SEQ ID NO: 9), ATVLNYLPK (SEQ ID NO: 10), RKEYEMK (SEQ ID NO: 11), and DTVIKPLLVEPEGLEK (SEQ ID NO: 12) for the 163 kDa protein;

one or more of DKVNSFFSTFK (SEQ ID NO: 13) and LTPYADEFKVK (SEQ ID NO: 14) for the 45 kDa protein;

one or more of RHPDLSIPELLR (SEQ ID NO: 15) and HFQNLGK (SEQ ID NO: 16) for afamin;

one or more of SASNMAIVDVK (SEQ ID NO: 6), RKEYEMK (SEQ ID NO: 11), ATVLNYLPK (SEQ ID NO: 10), FQVDNNNR (SEQ ID NO: 9), DTVIKPLLVEPEGLEK (SEQ ID NO: 12), TEHPFTVEEFVLPK (SEQ ID NO: 7), NEDSLVFVQTDK (SEQ ID NO: 5), DMYSFLEDMGLK (SEQ ID NO: 4), DLKPAIVK (SEQ ID NO: 3), MVSGFIPLKPTVK (SEQ ID NO: 2), LVHVEEPHTETVRK (SEQ ID NO: 1), and TTVMVK (SEQ ID NO: 8) for alpha-2-macroglobulin;

one or more of AHVDALR (SEQ ID NO: 17), SGRDYVSQFEGSALGK (SEQ ID NO: 18), PYLDDFQKK (SEQ ID NO: 19), YVSQFEGSALGK (SEQ ID NO: 20), LHELQEK (SEQ ID NO: 21), VSFLSALEEYTK (SEQ ID NO: 22), and QKLHELQEK (SEQ ID NO: 23) for apolipoprotein A-I;

one or more of DKVNSFFSTFK (SEQ ID NO: 13) and LTPYADEFKVK (SEQ ID NO: 14) for apolipoprotein A-IV;

one or more of MLETVR (SEQ ID NO: 24), AVSMPSFSILGSDVR (SEQ ID NO: 25), TEVIPPLIENR (SEQ ID NO: 26), and SVGFHLPSR (SEQ ID NO: 27) for apolipoprotein B-100;

one or more of GQIVFMNREPK (SEQ ID NO: 28), GPEVQLVAHSPWLK (SEQ ID NO: 29), SHALQLNNR (SEQ ID NO: 30), DFALLSLQVPLKDAK (SEQ ID NO: 31), and YIYGKPVQGVAYVR (SEQ ID NO: 32) for (8) complement C4B1;

one or more of AETGDKVYVHLK (SEQ ID NO: 33), and GPEEEHLGILGPVIWAEVGDTIR (SEQ ID NO: 34) for ceruloplasmin;

one or more of TLLSNLEEAK (SEQ ID NO: 35) and FMETVAEK (SEQ ID NO: 36) for clusterin isoform 1;

one or more of TLLSNLEEAK (SEQ ID NO: 35) and FMETVAEK (SEQ ID NO: 36) for clusterin;

one or more of FYYIYNEK (SEQ ID NO: 37), LMNIFLK (SEQ ID NO: 38), IPIEDGSGEVVLSR (SEQ ID NO: 39), IWDVVEK (SEQ ID NO: 40), TIYTPGSTVLYR (SEQ ID NO: 41), KGYTQQLAFR (SEQ ID NO: 42), RIPIEDGSGEVVLSR (SEQ ID NO: 43), VQLSNDFDEYIMAIEQTIK (SEQ ID NO: 44), RQGALELIKK (SEQ ID NO: 45), AAVYHHFISDGVRK (SEQ ID NO: 46), and YYTYLIMNK (SEQ ID NO: 47) for complement C3;

one or more of GPEVQLVAHSPWLK (SEQ ID NO: 29), SHALQLNNR (SEQ ID NO: 30), DFALLSLQVPLKDAK (SEQ ID NO: 31), YIYGKPVQGVAYVR (SEQ ID NO: 32), and GQIVFMNREPK (SEQ ID NO: 28) for complement C4;

one or more of GPEVQLVAHSPWLK (SEQ ID NO: 29), SHALQLNNR (SEQ ID NO: 30), DFALLSLQVPLKDAK (SEQ ID NO: 31), YIYGKPVQGVAYVR (SEQ ID NO: 32), and GQIVFMNREPK (SEQ ID NO: 28) for complement C4A;

one or more of YIYGKPVQGVAYVR (SEQ ID NO: 32), GQIVFMNREPK (SEQ ID NO: 28), SHALQLNNR (SEQ ID NO: 30), GPEVQLVAHSPWLK (SEQ ID NO: 29), and DFALLSLQVPLKDAK (SEQ ID NO: 31) for complement C4B;

one or more of DSHSLTTNIMEILR (SEQ ID NO: 48), GLIDEVNQDFTNR (SEQ ID NO: 49), and LKNSLFEYQK (SEQ ID NO: 50) for FGA protein;

one or more of HVVPNEVVVQR (SEQ ID NO: 51) and TASDFITK (SEQ ID NO: 52) for gelsolin isoform b;

one or more of HVVPNEVVVQR (SEQ ID NO: 51) and TASDFITK (SEQ ID NO: 52) for gelsolin;

one or more of LWWLDLK (SEQ ID NO: 53), RLWWLDLK (SEQ ID NO: 54), and GDKVWVYPPEKK (SEQ ID NO: 55) for hemopexin;

one or more of DSPVLIDFFEDTER (SEQ ID NO: 56), ADLFYDVEALDLESPK (SEQ ID NO: 57) for histidine-rich glycoprotein;

one or more of RLDGSVDFK (SEQ ID NO: 58) and TSTADYAMFK (SEQ ID NO: 59) for Hypothetical protein DKFZp779N0926;

one or more of FYNQVSTPLLR (SEQ ID NO: 60), SLAPTAAAK (SEQ ID NO: 61), and TILDDLR (SEQ ID NO: 62) for Inter-alpha-trypsin inhibitor heavy chain H2 precursor;

one or more of MVSGFIPLKPTVK (SEQ ID NO: 2), DLKPAIVK (SEQ ID NO: 3), and ATVLNYLPK (SEQ ID NO: 10) for pregnancy zone protein;

one or more of LKNSLFEYQK (SEQ ID NO: 50), DSHSLTTNIMEILR (SEQ ID NO: 48) and GLIDEVNQDFTNR (SEQ ID NO: 49) for Similar to fibrinogen, A alpha polypeptide;

one or more of NVVFVIDK (SEQ ID NO: 63), LGVYELLLK (SEQ ID NO: 64) and ETLFSVMPGLK (SEQ ID NO: 65) for Splice Isoform 1 of Inter-alpha-trypsin inhibitor heavy chain H4;

one or more of LGVYELLLK (SEQ ID NO: 64), ETLFSVMPGLK (SEQ ID NO: 65), and NVVFVIDK (SEQ ID NO: 63) for Splice Isoform 2 of Inter-alpha-trypsin inhibitor heavy chain H4;

one or more of MELERPGGNEITR (SEQ ID NO: 66), LKNSLFEYQK (SEQ ID NO: 50), DSHSLTTNIMEILR (SEQ ID NO: 48), TVIGPDGHKEVTK (SEQ ID NO: 67), and GLIDEVNQDFTNR (SEQ ID NO: 49) for Splice Isoform Alpha of Fibrinogen alpha/alpha-E chain;

one or more of LKNSLFEYQK (SEQ ID NO: 50), DSHSLTTNIMEILR (SEQ ID NO: 48), MELERPGGNEITR (SEQ ID NO: 66), GLIDEVNQDFTNR (SEQ ID NO: 49), and TVIGPDGHKEVTK (SEQ ID NO: 67) for Splice Isoform Alpha-E of Fibrinogen alpha/alpha-E chain;

one or more of RLDGSVDFK (SEQ ID NO: 58) and TSTADYAMFK (SEQ ID NO: 59) and Splice Isoform Gamma-A of Fibrinogen gamma chain;

one or more of RLDGSVDFK (SEQ ID NO: 58) and TSTADYAMFK (SEQ ID NO: 59) for Splice Isoform Gamma-B of Fibrinogen gamma chain; and one or more of ELPEHTVK (SEQ ID NO: 68), KFPSGTFEQVSQLVK (SEQ ID NO: 69), THLPEVFLSK (SEQ ID NO: 70), and HLSLLTTLSNR (SEQ ID NO: 71) for Vitamin D-binding protein.

3. The method of claim 1, wherein determining if the proteins are upregulated or downregulated relative to a subject not having type II diabetes mellitus comprises comparing the quantity of the analyzed proteins in the serum or blood plasma sample to a reference value representing a quantity of the proteins in a subject not having type II diabetes mellitus.

4. The method of claim 1, wherein analyzing comprises analyzing the serum or blood plasma sample using liquid chromatography/mass spectrometry.

* * * * *

SEQUENCE LISTING

```
<160> NUMBER OF SEQ ID NOS: 33

<210> SEQ ID NO 1
<211> LENGTH: 14
<212> TYPE: PRT
<213> ORGANISM: Homo sapiens

<400> SEQUENCE: 1

Leu Val His Val Glu Glu Pro His Thr Glu Thr Val Arg Lys
1               5                   10

<210> SEQ ID NO 2
<211> LENGTH: 13
<212> TYPE: PRT
<213> ORGANISM: Homo sapiens

<400> SEQUENCE: 2

Met Val Ser Gly Phe Ile Pro Leu Lys Pro Thr Val Lys
1               5                   10

<210> SEQ ID NO 3
<211> LENGTH: 103
<212> TYPE: PRT
<213> ORGANISM: Homo sapiens

<400> SEQUENCE: 3

Asp Leu Lys Pro Ala Ile Val Lys Asp Met Tyr Ser Phe Leu Glu Asp
1               5                   10                  15

Met Gly Leu Lys Asn Glu Asp Ser Leu Val Phe Val Gln Thr Asp Lys
            20                  25                  30

Ser Ala Ser Asn Met Ala Ile Val Asp Val Lys Thr Glu His Pro Phe
        35                  40                  45

Thr Val Glu Glu Phe Val Leu Pro Lys Thr Thr Val Met Val Lys Phe
    50                  55                  60

Gln Val Asp Asn Asn Arg Ala Thr Val Leu Asn Tyr Leu Pro Lys
65                  70                  75                  80

Arg Lys Glu Tyr Glu Met Lys Asp Thr Val Ile Lys Pro Leu Leu Val
                85                  90                  95

Glu Pro Glu Gly Leu Glu Lys
            100

<210> SEQ ID NO 4
<211> LENGTH: 22
<212> TYPE: PRT
<213> ORGANISM: Homo sapiens

<400> SEQUENCE: 4

Asp Lys Val Asn Ser Phe Phe Ser Thr Phe Lys Leu Thr Pro Tyr Ala
1               5                   10                  15
```

```
Asp Glu Phe Lys Val Lys
            20

<210> SEQ ID NO 5
<211> LENGTH: 19
<212> TYPE: PRT
<213> ORGANISM: Homo sapiens

<400> SEQUENCE: 5

Arg His Pro Asp Leu Ser Ile Pro Glu Leu Leu Arg His Phe Gln Asn
1               5                   10                  15

Leu Gly Lys

<210> SEQ ID NO 6
<211> LENGTH: 130
<212> TYPE: PRT
<213> ORGANISM: Homo sapiens

<400> SEQUENCE: 6

Ser Ala Ser Asn Met Ala Ile Val Asp Val Lys Arg Lys Glu Tyr Glu
1               5                   10                  15

Met Lys Ala Thr Val Leu Asn Tyr Leu Pro Lys Phe Gln Val Asp Asn
            20                  25                  30

Asn Asn Arg Asp Thr Val Ile Lys Pro Leu Leu Val Glu Pro Glu Gly
        35                  40                  45

Leu Glu Lys Thr Glu His Pro Phe Thr Val Glu Phe Val Leu Pro
    50                  55                  60

Lys Asn Glu Asp Ser Leu Val Phe Val Gln Thr Asp Lys Asp Met Tyr
65                  70                  75                  80

Ser Phe Leu Glu Asp Met Gly Leu Lys Asp Leu Lys Pro Ala Ile Val
                85                  90                  95

Lys Met Val Ser Gly Phe Ile Pro Leu Lys Pro Thr Val Lys Leu Val
            100                 105                 110

His Val Glu Glu Pro His Thr Glu Thr Val Arg Lys Thr Thr Val Met
        115                 120                 125

Val Lys
    130

<210> SEQ ID NO 7
<211> LENGTH: 72
<212> TYPE: PRT
<213> ORGANISM: Homo sapiens

<400> SEQUENCE: 7

Ala His Val Asp Ala Leu Arg Ser Gly Arg Asp Tyr Val Ser Gln Phe
1               5                   10                  15

Glu Gly Ser Ala Leu Gly Lys Pro Tyr Leu Asp Asp Phe Gln Lys Lys
            20                  25                  30

Tyr Val Ser Gln Phe Glu Gly Ser Ala Leu Gly Lys Leu His Glu Leu
        35                  40                  45

Gln Glu Lys Val Ser Phe Leu Ser Ala Leu Glu Glu Tyr Thr Lys Gln
    50                  55                  60

Lys Leu His Glu Leu Gln Glu Lys
65                  70

<210> SEQ ID NO 8
<211> LENGTH: 22
<212> TYPE: PRT
<213> ORGANISM: Homo sapiens
```

```
<400> SEQUENCE: 8

Asp Lys Val Asn Ser Phe Phe Ser Thr Phe Lys Leu Thr Pro Tyr Ala
1               5                   10                  15

Asp Glu Phe Lys Val Lys
            20

<210> SEQ ID NO 9
<211> LENGTH: 41
<212> TYPE: PRT
<213> ORGANISM: Homo sapiens

<400> SEQUENCE: 9

Met Leu Glu Thr Val Arg Ala Val Ser Met Pro Ser Phe Ser Ile Leu
1               5                   10                  15

Gly Ser Asp Val Arg Thr Glu Val Ile Pro Pro Leu Ile Glu Asn Arg
            20                  25                  30

Ser Val Gly Phe His Leu Pro Ser Arg
        35                  40

<210> SEQ ID NO 10
<211> LENGTH: 63
<212> TYPE: PRT
<213> ORGANISM: Homo sapiens

<400> SEQUENCE: 10

Gly Gln Ile Val Phe Met Asn Arg Glu Pro Lys Gly Pro Glu Val Gln
1               5                   10                  15

Leu Val Ala His Ser Pro Trp Leu Lys Ser His Ala Leu Gln Leu Asn
            20                  25                  30

Asn Arg Asp Phe Ala Leu Leu Ser Leu Gln Val Pro Leu Lys Asp Ala
            35                  40                  45

Lys Tyr Ile Tyr Gly Lys Pro Val Gln Gly Val Ala Tyr Val Arg
        50                  55                  60

<210> SEQ ID NO 11
<211> LENGTH: 35
<212> TYPE: PRT
<213> ORGANISM: Homo sapiens

<400> SEQUENCE: 11

Ala Glu Thr Gly Asp Lys Val Tyr Val His Leu Lys Gly Pro Glu Glu
1               5                   10                  15

Glu His Leu Gly Ile Leu Gly Pro Val Ile Trp Ala Gly Val Gly Asp
            20                  25                  30

Thr Ile Arg
        35

<210> SEQ ID NO 12
<211> LENGTH: 18
<212> TYPE: PRT
<213> ORGANISM: Homo sapiens

<400> SEQUENCE: 12

Thr Leu Leu Ser Asn Leu Glu Glu Ala Lys Phe Met Glu Thr Val Ala
1               5                   10                  15

Glu Lys

<210> SEQ ID NO 13
<211> LENGTH: 18
<212> TYPE: PRT
<213> ORGANISM: Homo sapiens
```

```
<400> SEQUENCE: 13

Thr Leu Leu Ser Asn Leu Glu Glu Ala Lys Phe Met Glu Thr Val Ala
1               5                   10                  15

Glu Lys

<210> SEQ ID NO 14
<211> LENGTH: 125
<212> TYPE: PRT
<213> ORGANISM: Homo sapiens

<400> SEQUENCE: 14

Phe Tyr Tyr Ile Tyr Asn Glu Lys Leu Met Asn Ile Phe Leu Lys Ile
1               5                   10                  15

Pro Ile Glu Asp Gly Ser Gly Val Val Leu Ser Arg Ile Trp Asp
            20                  25                  30

Val Val Glu Lys Thr Ile Tyr Thr Pro Gly Ser Thr Val Leu Tyr Arg
        35                  40                  45

Lys Gly Tyr Thr Gln Gln Leu Ala Phe Arg Arg Ile Pro Ile Glu Asp
    50                  55                  60

Gly Ser Gly Glu Val Val Leu Ser Arg Val Gln Leu Ser Asn Asp Phe
65                  70                  75                  80

Asp Glu Tyr Ile Met Ala Ile Glu Gln Thr Ile Lys Arg Gln Gly Ala
                85                  90                  95

Leu Glu Leu Ile Lys Lys Ala Ala Val Tyr His His Phe Ile Ser Asp
            100                 105                 110

Gly Val Arg Lys Tyr Tyr Thr Tyr Leu Ile Met Asn Lys
        115                 120                 125

<210> SEQ ID NO 15
<211> LENGTH: 63
<212> TYPE: PRT
<213> ORGANISM: Homo sapiens

<400> SEQUENCE: 15

Gly Pro Glu Val Gln Leu Val Ala His Ser Pro Trp Leu Lys Ser His
1               5                   10                  15

Ala Leu Gln Leu Asn Asn Arg Asp Phe Ala Leu Leu Ser Leu Gln Val
            20                  25                  30

Pro Leu Lys Asp Ala Lys Tyr Ile Tyr Gly Lys Pro Val Gln Gly Val
        35                  40                  45

Ala Tyr Val Arg Gly Gln Ile Val Phe Met Asn Arg Glu Pro Lys
    50                  55                  60

<210> SEQ ID NO 16
<211> LENGTH: 63
<212> TYPE: PRT
<213> ORGANISM: Homo sapiens

<400> SEQUENCE: 16

Gly Pro Glu Val Gln Leu Val Ala His Ser Pro Trp Leu Lys Ser His
1               5                   10                  15

Ala Leu Gln Leu Asn Asn Arg Asp Phe Ala Leu Leu Ser Leu Gln Val
            20                  25                  30

Pro Leu Lys Asp Ala Lys Tyr Ile Tyr Gly Lys Pro Val Gln Gly Val
        35                  40                  45

Ala Tyr Val Arg Gly Gln Ile Val Phe Met Asn Arg Glu Pro Lys
    50                  55                  60
```

<210> SEQ ID NO 17
<211> LENGTH: 63
<212> TYPE: PRT
<213> ORGANISM: Homo sapiens

<400> SEQUENCE: 17

Tyr Ile Tyr Gly Lys Pro Val Gln Gly Val Ala Tyr Val Arg Gly Gln
1               5                   10                  15

Ile Val Phe Met Asn Arg Glu Pro Lys Ser His Ala Leu Gln Leu Asn
            20                  25                  30

Asn Arg Gly Pro Glu Val Gln Leu Val Ala His Ser Pro Trp Leu Lys
        35                  40                  45

Asp Phe Ala Leu Leu Ser Leu Gln Val Pro Leu Lys Asp Ala Lys
    50                  55                  60

<210> SEQ ID NO 18
<211> LENGTH: 37
<212> TYPE: PRT
<213> ORGANISM: Homo sapiens

<400> SEQUENCE: 18

Asp Ser His Ser Leu Thr Thr Asn Ile Met Glu Ile Leu Arg Gly Leu
1               5                   10                  15

Ile Asp Glu Val Asn Gln Asp Phe Thr Asn Arg Leu Lys Asn Ser Leu
            20                  25                  30

Phe Glu Tyr Gln Lys
        35

<210> SEQ ID NO 19
<211> LENGTH: 19
<212> TYPE: PRT
<213> ORGANISM: Homo sapiens

<400> SEQUENCE: 19

His Val Val Pro Asn Glu Val Val Val Gln Arg Thr Ala Ser Asp Phe
1               5                   10                  15

Ile Thr Lys

<210> SEQ ID NO 20
<211> LENGTH: 19
<212> TYPE: PRT
<213> ORGANISM: Homo sapiens

<400> SEQUENCE: 20

His Val Val Pro Asn Glu Val Val Val Gln Arg Thr Ala Ser Asp Phe
1               5                   10                  15

Ile Thr Lys

<210> SEQ ID NO 21
<211> LENGTH: 27
<212> TYPE: PRT
<213> ORGANISM: Homo sapiens

<400> SEQUENCE: 21

Leu Trp Trp Leu Asp Leu Lys Arg Leu Trp Trp Leu Asp Leu Lys Gly
1               5                   10                  15

Asp Lys Val Trp Val Tyr Pro Glu Lys Lys
            20                  25

<210> SEQ ID NO 22
<211> LENGTH: 30

```
<212> TYPE: PRT
<213> ORGANISM: Homo sapiens

<400> SEQUENCE: 22

Asp Ser Pro Val Leu Ile Asp Phe Phe Glu Asp Thr Glu Arg Ala Asp
1               5                   10                  15

Leu Phe Tyr Asp Val Glu Ala Leu Asp Leu Glu Ser Pro Lys
            20                  25                  30

<210> SEQ ID NO 23
<211> LENGTH: 19
<212> TYPE: PRT
<213> ORGANISM: Homo sapiens

<400> SEQUENCE: 23

Arg Leu Asp Gly Ser Val Asp Phe Lys Thr Ser Thr Ala Asp Tyr Ala
1               5                   10                  15

Met Phe Lys

<210> SEQ ID NO 24
<211> LENGTH: 27
<212> TYPE: PRT
<213> ORGANISM: Homo sapiens

<400> SEQUENCE: 24

Phe Tyr Asn Gln Val Ser Thr Pro Leu Leu Arg Ser Leu Ala Pro Thr
1               5                   10                  15

Ala Ala Ala Lys Thr Ile Leu Asp Asp Leu Arg
            20                  25

<210> SEQ ID NO 25
<211> LENGTH: 30
<212> TYPE: PRT
<213> ORGANISM: Homo sapiens

<400> SEQUENCE: 25

Met Val Ser Gly Phe Ile Pro Leu Lys Pro Thr Val Lys Asp Leu Lys
1               5                   10                  15

Pro Ala Ile Val Lys Ala Thr Val Leu Asn Tyr Leu Pro Lys
            20                  25                  30

<210> SEQ ID NO 26
<211> LENGTH: 37
<212> TYPE: PRT
<213> ORGANISM: Homo sapiens

<400> SEQUENCE: 26

Leu Lys Asn Ser Leu Phe Glu Tyr Gln Lys Asp Ser His Ser Leu Thr
1               5                   10                  15

Thr Asn Ile Met Glu Ile Leu Arg Gly Leu Ile Asp Glu Val Asn Gln
            20                  25                  30

Asp Phe Thr Asn Arg
            35

<210> SEQ ID NO 27
<211> LENGTH: 28
<212> TYPE: PRT
<213> ORGANISM: Homo sapiens

<400> SEQUENCE: 27

Asn Val Val Phe Val Ile Asp Lys Leu Gly Val Tyr Glu Leu Leu Leu
1               5                   10                  15
```

Lys Glu Thr Leu Phe Ser Val Met Pro Gly Leu Lys
            20                  25

<210> SEQ ID NO 28
<211> LENGTH: 28
<212> TYPE: PRT
<213> ORGANISM: Homo sapiens

<400> SEQUENCE: 28

Leu Gly Val Tyr Glu Leu Leu Lys Glu Thr Leu Phe Ser Val Met
1               5                   10                  15

Pro Gly Leu Lys Asn Val Val Phe Val Ile Asp Lys
            20                  25

<210> SEQ ID NO 29
<211> LENGTH: 63
<212> TYPE: PRT
<213> ORGANISM: Homo sapiens

<400> SEQUENCE: 29

Met Glu Leu Glu Arg Pro Gly Gly Asn Glu Ile Thr Arg Leu Lys Asn
1               5                   10                  15

Ser Leu Phe Glu Tyr Gln Lys Asp Ser His Ser Leu Thr Thr Asn Ile
            20                  25                  30

Met Glu Ile Leu Arg Thr Val Ile Gly Pro Asp Gly His Lys Glu Val
        35                  40                  45

Thr Lys Gly Leu Ile Asp Glu Val Asn Gln Asp Phe Thr Asn Arg
    50                  55                  60

<210> SEQ ID NO 30
<211> LENGTH: 63
<212> TYPE: PRT
<213> ORGANISM: Homo sapiens

<400> SEQUENCE: 30

Leu Lys Asn Ser Leu Phe Glu Tyr Gln Lys Asp Ser His Ser Leu Thr
1               5                   10                  15

Thr Asn Ile Met Glu Ile Leu Arg Met Glu Leu Glu Arg Pro Gly Gly
            20                  25                  30

Asn Glu Ile Thr Arg Gly Leu Ile Asp Glu Val Asn Gln Asp Phe Thr
        35                  40                  45

Asn Arg Thr Val Ile Gly Pro Asp Gly His Lys Glu Val Thr Lys
    50                  55                  60

<210> SEQ ID NO 31
<211> LENGTH: 19
<212> TYPE: PRT
<213> ORGANISM: Homo sapiens

<400> SEQUENCE: 31

Arg Leu Asp Gly Ser Val Asp Phe Lys Thr Ser Thr Ala Asp Tyr Ala
1               5                   10                  15

Met Phe Lys

<210> SEQ ID NO 32
<211> LENGTH: 19
<212> TYPE: PRT
<213> ORGANISM: Homo sapiens

<400> SEQUENCE: 32

Arg Leu Asp Gly Ser Val Asp Phe Lys Thr Ser Thr Ala Asp Tyr Ala
1               5                   10                  15

Met Phe Lys

<210> SEQ ID NO 33
<211> LENGTH: 44
<212> TYPE: PRT
<213> ORGANISM: Homo sapiens

<400> SEQUENCE: 33

Glu Leu Pro Glu His Thr Val Lys Lys Phe Pro Ser Gly Thr Phe Glu
1               5                   10                  15

Gln Val Ser Gln Leu Val Lys Thr His Leu Pro Glu Val Phe Leu Ser
            20                  25                  30

Lys His Leu Ser Leu Leu Thr Thr Leu Ser Asn Arg
        35                  40